United States Patent
Page et al.

(10) Patent No.: US 10,252,053 B2
(45) Date of Patent: Apr. 9, 2019

(54) ELECTRONIC NERVE STIMULATION

(71) Applicant: University of Utah Research Foundation, Salt Lake City, UT (US)

(72) Inventors: David Page, Salt Lake City, UT (US); Christopher Duncan, Salt Lake City, UT (US); David Kluger, Salt Lake City, UT (US); Zachary Kagan, Salt Lake City, UT (US); Gregory Clark, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/476,016

(22) Filed: Mar. 31, 2017

(65) Prior Publication Data
US 2017/0281941 A1    Oct. 5, 2017

Related U.S. Application Data (60) Provisional application No. 62/316,244, filed on Mar. 31, 2016.

(51) Int. Cl.
*A61N 1/00* (2006.01)
*A61N 1/36* (2006.01)
*A61N 1/04* (2006.01)

(52) U.S. Cl.
CPC ........ *A61N 1/36021* (2013.01); *A61N 1/0456* (2013.01); *A61N 1/36034* (2017.08); *A61N 1/0472* (2013.01); *A61N 1/3603* (2017.08)

(58) Field of Classification Search
CPC ................................. A61N 1/36021
USPC ........................................................ 607/46
See application file for complete search history.

(56) References Cited

U.S. PATENT DOCUMENTS

| | | |
|---|---|---|
| 4,014,347 A | 3/1977 | Halleck et al. |
| 4,155,366 A | 5/1979 | Di Mucci |
| 4,305,402 A | 12/1981 | Katims |
| 4,924,880 A | 5/1990 | O'Neill et al. |
| 5,052,391 A | 10/1991 | Silberstone et al. |
| 6,161,044 A | 12/2000 | Silverstone |

(Continued)

FOREIGN PATENT DOCUMENTS

| | | |
|---|---|---|
| WO | WO 2015/196164 A2 | 12/2015 |

OTHER PUBLICATIONS

Kilgore et al.; "Reversible Nerve Conduction Block Using Kilohertz Frequency Alternating Current"; Neuromodulation; NIH Public Access Author Manuscript; Apr. 2014; p. 242-255; vol. 17(3); doi:10.1111/ner.12100.

(Continued)

*Primary Examiner* — Nadia A Mahmood
(74) *Attorney, Agent, or Firm* — Thorpe North & Western, L.L.P.

(57) ABSTRACT

A technology is described for an electronic nerve stimulation system. The electronic nerve stimulation system can include a stimulation device operable to generate a high-frequency alternating current. The electronic nerve stimulation system can include one or more wearable electrodes operable to apply the high-frequency alternating current from the stimulation device to peripheral nerves to provide an electrical stimulation of neuronal tissue to treat pain. The one or more wearable electrodes can interface with the stimulation device via a connection system.

23 Claims, 7 Drawing Sheets

(56) References Cited

U.S. PATENT DOCUMENTS

| | | | |
|---|---|---|---|
| 7,389,145 | B2 | 6/2008 | Kilgore et al. |
| 9,101,766 | B2 | 8/2015 | Nekhendzy |
| 9,205,258 | B2 | 12/2015 | Simon et al. |
| 9,242,085 | B2 | 1/2016 | Hershey et al. |
| 2002/0077670 | A1 | 6/2002 | Archer et al. |
| 2011/0098777 | A1 | 4/2011 | Silverstone |
| 2014/0228837 | A1 | 8/2014 | Giovangrandi et al. |
| 2014/0249597 | A1 | 9/2014 | Fang et al. |
| 2014/0296934 | A1 | 10/2014 | Gozani et al. |
| 2014/0324119 | A1 | 10/2014 | Farone |
| 2014/0336728 | A1 | 11/2014 | Franke et al. |
| 2014/0379044 | A1 | 12/2014 | Walker et al. |
| 2015/0088224 | A1 | 3/2015 | Goldwasser et al. |
| 2015/0174397 | A1 | 6/2015 | Bhadra et al. |
| 2015/0321000 | A1 | 11/2015 | Rosenbluth et al. |
| 2015/0328461 | A1* | 11/2015 | Charlesworth .... A61N 1/36014 607/45 |
| 2015/0374983 | A1 | 12/2015 | Simon et al. |
| 2016/0008602 | A1 | 1/2016 | Perryman et al. |

OTHER PUBLICATIONS

Fish et al.; "Conduction of Electrical Current to and Through the Human Body: A Review"; Eplasty, Journal of Plastic Surgery; Oct. 12, 2009; p. 407-421; vol. 9(44); https://www.ncbi.nlm.nih.gov/pmc/articles/PMC2763825/.

Christensen et al.; "Cutaneous Depth of the Supraorbital Nerve: A Cadaveric Anatomic Study With Clinical Applications to Dermatology"; Dermatologic Surgery; Dec. 2014; p. 1342-1348; vol. 40(12); Lippincort Williams & Wilkins; https://www.ncbi.nlm.nih.gov/pubmed/25357169/.

\* cited by examiner

ELECTRONIC NERVE STIMULATION

RELATED APPLICATION(S)

This application claims the benefit of U.S. Provisional Application No. 62/316,244, filed Mar. 31, 2016 which is incorporated herein by reference.

BACKGROUND

For purposes of this application, electrical stimulation of neurons is a procedure that uses an electrical current to stimulate neuronal tissues in order treat pain. Peripheral nerve stimulation (PNS) and spinal cord stimulation (SCS) are two types of electrical stimulation of neurons. In both cases, a small pulse generator sends electrical pulses to the nerves (in PNS) or to the spinal cord (in SCS). The electrical pulses can interfere with neuronal electrical impulses, thereby reducing a sensation of pain in a subject. One or more electrodes can be inserted under the patient's skin (i.e., percutaneously). The electrodes can be attached to the subject's nerves or spinal canal. The electrodes can be connected to a stimulator, which produce the electrical pulses. The delivery of electrical pulses from the stimulator to the electrodes can reduce the subject's pain in areas directly or indirectly innervated by neurons stimulated by the electrodes. Despite some advances with such technologies, current options tend to have limited effectiveness or can result in undesirable loss of sensation or other side-effects.

SUMMARY

A technology is described for delivering high-frequency alternating current to neuronal tissues via electrodes to achieve pain blocking. In one example, there is provided an electronic nerve stimulation system comprising a stimulation device and one or more wearable electrodes. The stimulation device can be operable to generate a high-frequency alternating current. The one or more wearable electrodes operable to apply the high-frequency alternating current from the stimulation device to peripheral nerves to provide an electrical stimulation to neuronal tissue, where the one or more wearable electrodes interface with the stimulation device via a unique connection system.

In one example of the electronic nerve stimulation system, the stimulation device is further operable to generate the high-frequency alternating current to be a waveform ranging from 10 to 50 kilohertz (kHz).

In one example of the electronic nerve stimulation system, the stimulation device is further operable to generate the high-frequency alternating current to be a waveform in a 0-50 milliamp (mA) range and in some cases from 0 to 10 mA range, wherein the high-frequency alternating current is applied across a skin or body resistance of 10 ohms ($\Omega$) to 50 kilo-ohms (k$\Omega$), and in some cases from 1 kOhm to 10 kOhm.

In one example of the electronic nerve stimulation system, the high-frequency alternating current is applied to peripheral nerves that are less than two centimeters (cm) from a skin surface, and in many cases less than 0.5 cm from the skin surface.

In one example of the electronic nerve stimulation system, the electronic nerve stimulation system further comprises a power supply that provides direct current or alternating current to the stimulation device for generation of the high-frequency alternating current. Although other current sources can be used, in one example, the DC or AC is provided via batteries or via a wall-plug adapter or via both batteries and wall-plug adapter.

In one example of the electronic nerve stimulation system, the electronic nerve stimulation system further comprises a user interface that enables adjustment of at least one of a frequency and amplitude of the high-frequency alternating current.

In one example of the electronic nerve stimulation system, the stimulation device is further operable to implement a pre-programmed frequency modulation pattern when generating the high-frequency alternating current.

In one example of the electronic nerve stimulation system, the wearable electrodes are tailored to peripheral nerves in specific body locations.

In one example of the electronic nerve stimulation system, the high-frequency alternating current is applied to the peripheral nerves to stimulate neuronal tissue to cause at least one of the following: pain blocking, sensation blocking and muscle activation.

In one example of the electronic nerve stimulation system, the stimulation device is operable to generate the high-frequency alternating current via current-control circuitry that includes an amplifier, an oscillator circuit, a rectifier and a smoothing filter.

In one example of the electronic nerve stimulation system, the stimulation device is operable to generate the high-frequency alternating current via current-control circuitry in which feedback via two operational amplifiers creates a voltage-controlled current source.

In one example of the electronic nerve stimulation system, the wearable electrodes include at least one of: finger electrodes, toe electrodes, arm electrodes, leg electrodes, face electrodes, neck electrodes and penis electrodes.

In one example of the electronic nerve stimulation system the stimulation device is operable to generate the high-frequency alternating current via high frequency transcutaneous circuitry that includes a power supply, an oscillator generator, a gain amplifier and a high voltage current pump.

In one example, there is provided a system for blocking peripheral nerve transmission, the system comprising a power source, a stimulation device, and one or more wearable electrodes. The stimulation device operable to generate a high-frequency alternating current using current provided from the power source. The one or more wearable electrodes communicatively coupled to the simulation device via lead wires and connectors. The wearable electrodes are operable to apply the high-frequency alternating current received from the stimulation device to peripheral nerves of a subject for the blocking of peripheral nerve transmission, where the one or more wearable electrodes include non-invasive, non-penetrating electrodes.

In one example of the system for blocking peripheral nerve transmission, the stimulation device is operable to generate the high-frequency alternating current to be a sinusoidally varying, constant amplitude current waveform through a variable impedance load.

In one example of the system for blocking peripheral nerve transmission, the stimulation device is operable to generate the high-frequency alternating current to be adjustable from 9 k to 50 k hertz (Hz) and from 0 to 20 milliamps (mA) via potentiometers.

In one example of the system for blocking peripheral nerve transmission, the power source provides direct current or alternating current to the stimulation device for generation of the high-frequency alternating current.

In one example of the system for blocking peripheral nerve transmission, the stimulation device is operable to generate the high-frequency alternating current via high frequency transcutaneous circuitry that includes a power supply, an oscillator generator, a gain amplifier and a high voltage current pump.

In one example of the system for blocking peripheral nerve transmission, the one or more wearable electrodes are not surgically implanted in the subject.

In one example, there is provided a method for electronically blocking peripheral nerve transmission, the method including receiving a current from a power source, wherein the current includes direct current or alternating current. The method can further include generating a high-frequency alternating current using the current provided from the power source. The method can also include providing the high-frequency alternating current to one or more wearable electrodes, wherein the wearable electrodes are operable to apply the high-frequency current to peripheral nerves of a subject for the blocking of peripheral nerve transmission. The one or more wearable electrodes include non-invasive, non-penetrating electrodes.

In one example of the method for electronically blocking peripheral nerve transmission, the high-frequency alternating current is generated to be a sinusoidally varying, constant amplitude current waveform through a variable impedance load.

In one example of the method for electronically blocking peripheral nerve transmission, the high-frequency alternating current is generated to be adjustable from 9 k to 50 k hertz (Hz) and from 0 to 20 milliamps (mA) via potentiometers.

In one example of the method for electronically blocking peripheral nerve transmission, the high-frequency alternating current is generated using a pre-programmed frequency modulation pattern.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a filter" includes reference to one or more of such components and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

The present technology relates to an electronic nerve stimulation system that functions to block transmission of pain sensation by stimulating neuronal tissue within peripheral nerves. The electronic nerve stimulation system can provide a defined amount of alternating current to a subject's nerves, which can interfere with neuron impulses and reduce a sensation of pain for the subject. The electronic nerve stimulation system can include non-invasive, non-penetrating electrodes and/or minimally-invasive, penetrating electrodes that breaches only an outermost, high-impedance epidermal layer of the skin. The electrodes may or may not be disposable. The electrodes can be coupled to a high-frequency electronic stimulator that provides high-frequency electrical stimulation to peripheral nerves via the non-invasive and/or minimally-invasive electrodes. The electrodes can interface with the high-frequency electronic stimulator via a connection system. The high-frequency electronic stimulator can be portable or non-portable (e.g., for use inside or outside a clinic). In the case of a portable system, the stimulator can be powered by an external battery capable of delivering voltage sufficient to deliver current to targeted neuronal tissue. Notably, nerves are a collection of neuronal axons. The system can be carried and worn by a patient. Similarly, when the stimulator is non-portable, the stimulator can be powered from an outlet. Medical-grade isolation circuitry can be included in the non-portable stimulator to prevent errant spikes in wall power from reaching a patient and causing bodily harm. The electronic nerve stimulation system can achieve chronic (long-term) or acute (short-term) blocking of peripheral nerve transmission of pain sensation. In other words, the electronic nerve stimulation system can provide both chronic (long-term) or acute (short-term) pain relief and general sensory and/or motor block.

In one example, non-invasive, non-penetrating electrodes can be placed on an outer surface of a body (e.g., skin) for delivering high-frequency (e.g., 1-100 kHz) alternating current to tissues and nerves. Additionally or alternatively, minimally-invasive, penetrating electrodes can be placed through a body surface (e.g., skin) for delivering high frequency (e.g., 1-100 kHz) alternating current to tissues and nerves. In addition, both portable and non-portable electronic stimulators can be attached to the electrodes to produce high-frequency alternating current sufficient for nerve block. As a result, nerve transmission can be blocked via peripheral nerves at various potential locations across the body. This will allow for blocking pain, general sensation, and/or muscle activation. In some cases, the nerve transmission can be selectively blocked to allow for blocking pain without also blocking muscle activation, for example. This can be achieved through varying the stimulator's output frequency or targeting nerves that only carry sensory information that travels towards the brain.

In one example, unlike previous approaches, the present technology provides the ability to perform high frequency nerve-block at various locations on the body using non-invasive and/or minimally invasive approaches, which can eliminate surgical implantation of electrodes. In addition, previous solutions used stimulation amplitudes and electrode configurations for the purpose of low-level, background pain treatment, whereas the present technology can provide complete sensory and pain blockage.

As an example, noninvasive, non-penetrating electrodes can be placed on a surface of a pinky finger. The electrodes can be used to produce a full block of nerve transmission on the pinky finger. This full block can include a blocking of general sensation from the pinky finger, including sensation of temperature changes, stroking, pressing, and needle poking. The full block of nerve transmission can essentially numb different parts of the body without injected anesthetics.

In one example, the electronic nerve stimulation system can be used for a 'needle-free' alternative to traditional injected local anesthetics (e.g., lidocaine) for cases such as finger laceration repair (e.g., stitches) or for infant or adult circumcision. In contrast to lidocaine injections, which can cause discomfort from a needle stick, the electronic nerve stimulation system can provide pain blockage that is comfortable and non-painful. In another example, the electronic nerve stimulation system can be used for numbing and pain block in scenarios where patients are currently expected to endure pain, such as numbing the skin prior to injecting a vaccine or insulin shot. In yet another example, the electronic nerve stimulation system can provide in-clinic and out-of-clinic use of nerve block for treating chronic pain conditions. For example, the electronic nerve stimulation system can provide relief to diabetic patients who suffer from chronic neuropathic pain in the hands and the feet, or for patients suffering from occipital neuralgia or trauma-induced nerve damage. Such pain blocking technology can provide chronic relief for patients suffering from nerve damage or phantom pain or chronic neuropathy (e.g. diabetic patients). In addition, such non-invasive technology can replace common painful injections associated with numbing the mouth prior to dental procedures and for other possible targets on the body.

In one example, nerve block can be achieved when the electrodes are sufficiently close to a peripheral nerve being targeted. For example, nerve block can be achieved when the nerve is close to the surface of the skin or external tissue, or when minimally-invasive, penetrating electrodes are inserted and placed near the nerve or target neuronal tissue. Non-invasive or minimally-invasive pain block can be applied to numb a body area prior to procedures where patients are currently expected to endure pain, such as prior to injection of a vaccine or insulin shot or insertion of an IV catheter. While there may be some peripheral nerve targets that are inaccessible for such interventions, a number of useful targets can be accessible, such as nerves in the hands, arms, penis, neck, and face. Some peripheral nerve targets can be unacceptable for such interventions, such as nerve targets close to the heart.

Figure 1:
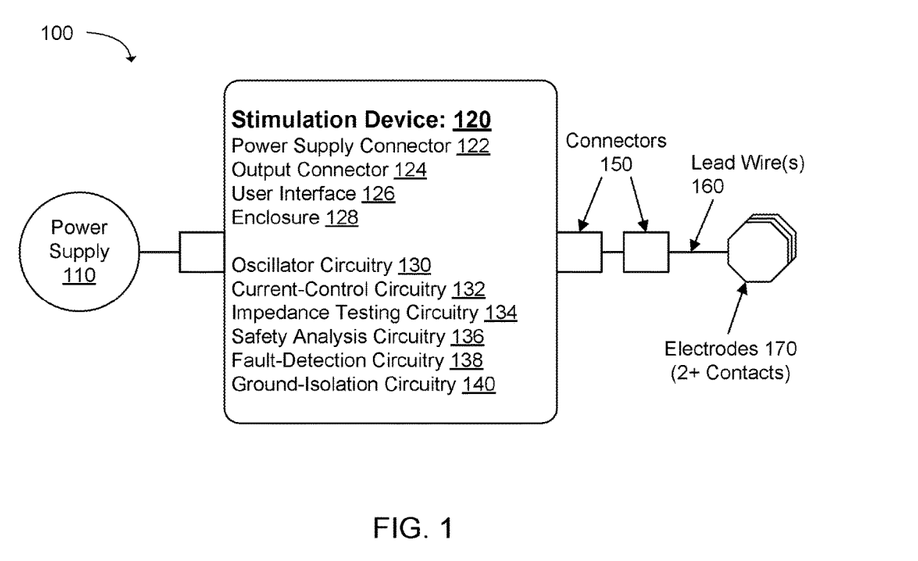
FIG. 1 illustrates an electronic nerve stimulation system in accordance with an example.

FIG. 1 illustrates an exemplary electronic nerve stimulation system 100. The electronic nerve stimulation system 100 can be configured to block nerve transmission to peripheral nerves by targeted stimulation of neuronal tissue, thereby reducing a sensation of pain in a subject. The electronic nerve stimulation system 100 can include a power supply 110, a stimulation device 120, connectors 150, lead wires 160 and one or more electrodes 170. The stimulation device 120 can provide a defined amount of high-frequency alternating current to the electrodes 170 via the lead wires 160. In a specific example, the stimulation device 120 can provide a sinusoidally varying, constant amplitude current waveform through a variable impedance load. The connectors 150 can enable the stimulation device 120 to connect to the electrodes 170. The electrodes 170 (e.g., wearable electrodes) can be placed on or within a body part of the subject. The delivery of the high-frequency alternating current to the electrodes 170 can cause nerve transmissions to be blocked in a vicinity of the electrodes 170, thereby reducing the sensation of pain in the subject. In addition, by placing the electrodes 170 on or within the body part of the subject, sensation blocking and/or muscle activation can be achieved for the subject. The electrodes 170 can be non-invasive, non-penetrating electrodes and/or minimally-invasive, penetrating electrodes.

In one example, the electronic nerve stimulation system 100 can operate to block nerve transmissions for cases that are not disorders (e.g., blocking sensation during surgical procedures, needle pricks, and other procedures). The electronic nerve stimulation system 100 can perform transcutaneous stimulation for blocking nerve transmission prior to certain procedures (e.g., needle pricks, tattoos, surgical procedures). The electronic nerve stimulation system 100 can aim for nerve and neuronal tissue targets that are superficial (e.g., less than 2 cm) beneath the skin using non-invasive or minimally-invasive electrodes 170. However, as a general rule, the nerve and neuronal tissue targets can be less than 2 cm, often less than 1 cm and in some cases less than 0.5 cm.

In one example, the power supply 110 can provide up to ±300 volts (V) amplitude, which can be either direct current (DC) or alternating current (AC) in the range of 0.01 Hz to 50 kHz. The power supply 110 can source at least 30-50 mA across a subject's skin. In addition, the power supply 110 can be provided via batteries or via a wall-plug adaptor or both (e.g., wall-plug adaptor with batteries for backup), although other power sources can be used.

In one example, the stimulation device 120 can include a power supply connector 122, an output connector 124, a user interface 126 and an enclosure 128. The power supply connector 122 can connect the stimulation device 120 to the power supply 110. The output connector 124 can connect the stimulation device 120 to the electrodes 170. The user interface 126 can include various buttons, knobs, light emitting diode (LED) indicator lights and/or a digital display. The user interface 126 can include controls to power on or off the stimulation device 120. The user interface 126 can include controls adjust or set a frequency and amplitude (e.g., voltage and/or current). The user interface 126 can include controls to run impedance tests, report impedance test results and indicate faults. In addition, the enclosure 128 can provide a housing or casing for components in the stimulation device 120 (except perhaps a connection to wall power, which would be external).

In one example, the stimulation device 120 can further include oscillator circuitry 130. The oscillator circuitry 130 can produce the high-frequency alternating current, in part, using the DC/AC received from the power supply 110. The stimulation device 120 can generate the high-frequency alternating current to be a 10-50 kHz waveform and be in a 0-50 milliamp (mA) range. The high-frequency alternating current may or may not be charge balanced. The oscillator circuitry 130 can include pre-programmed frequency-modulation patterns (e.g., ramp from 50 kHz down to 10 kHz over several seconds). In other words, the oscillator circuitry 130 can implement these pre-programmed frequency-modulation patterns when generating the high-frequency alternating current. In one example, the oscillator circuitry can be a Bubba oscillator. However, any circuit capable of developing a sinusoidal signal with distortion less than 3% may also be used.

Furthermore, the stimulation device 120 can include current-control circuitry 132, impedance testing circuitry 134, safety analysis circuitry 136, fault-detection circuitry 138, and ground-isolation circuitry 140. The current-control circuitry 132 can set a stimulation current amplitude in the 0-50 mA range across a resistance (e.g., skin/body) of 10Ω to 50 kΩ. The impedance testing circuitry 134 can test impedance (e.g., skin impedance) across combinations of electrode contacts. The safety analysis circuitry 136 can analyze results of an impedance test and determine whether usage of the stimulation device 120 is safe, which can be indicated to a user via the user interface 126. Safe thresholds can be preset or adjustable. However, as a general guideline safe thresholds (i.e. maximum) can be 10 mA and in some cases 1 mA. The fault detection circuitry 138 can monitor an output for signals of a short circuit, impedance spike, etc. and disconnect the power supply 110 when faults are detected. The ground isolation circuitry 140 (which is employed when wall power is used) can isolate the stimulation device 120, electrodes 170 and a patient from a wall ground connection for safety purposes.

Figure 2:
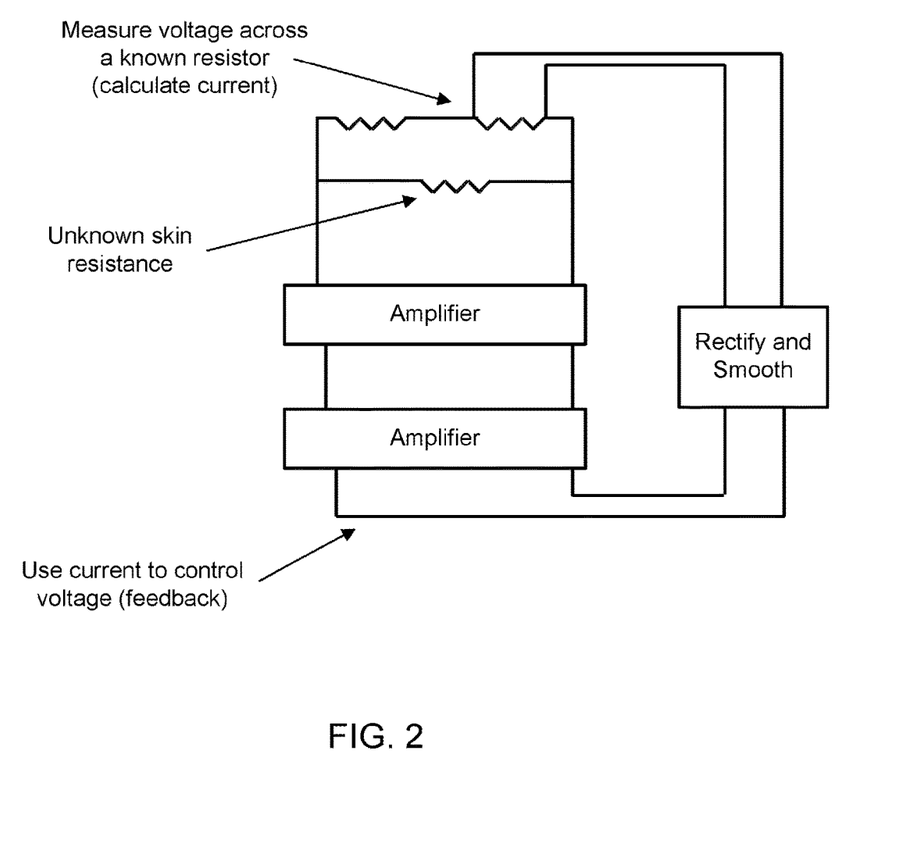
FIG. 2 illustrates current-control circuitry for an electronic nerve stimulation system in accordance with an example.

FIG. 2 illustrates an example of current-control circuitry for an electronic nerve stimulation system. The current-control circuitry can be included in a stimulation device of the electronic nerve stimulation system. The current-control circuitry can set a stimulation current amplitude in the 0-50 mA range across a resistance (e.g., skin/body) of 10Ω to 50 kΩ. The current-control circuitry can include one or more amplifiers, an oscillator circuit and a rectification and smoothing component such as a smoothing filter. Non-limiting examples of smoothing filters can include adjustable band-pass filters with a Q factor greater than ½. In one example, the current-control circuitry can additionally function as impedance-testing circuitry. As shown in FIG. 2, a voltage can be measured across a known resistor to calculate a current. The current-control circuitry can include an unknown skin resistance, and current can be used to control the voltage as a feedback signal.

Figure 3:
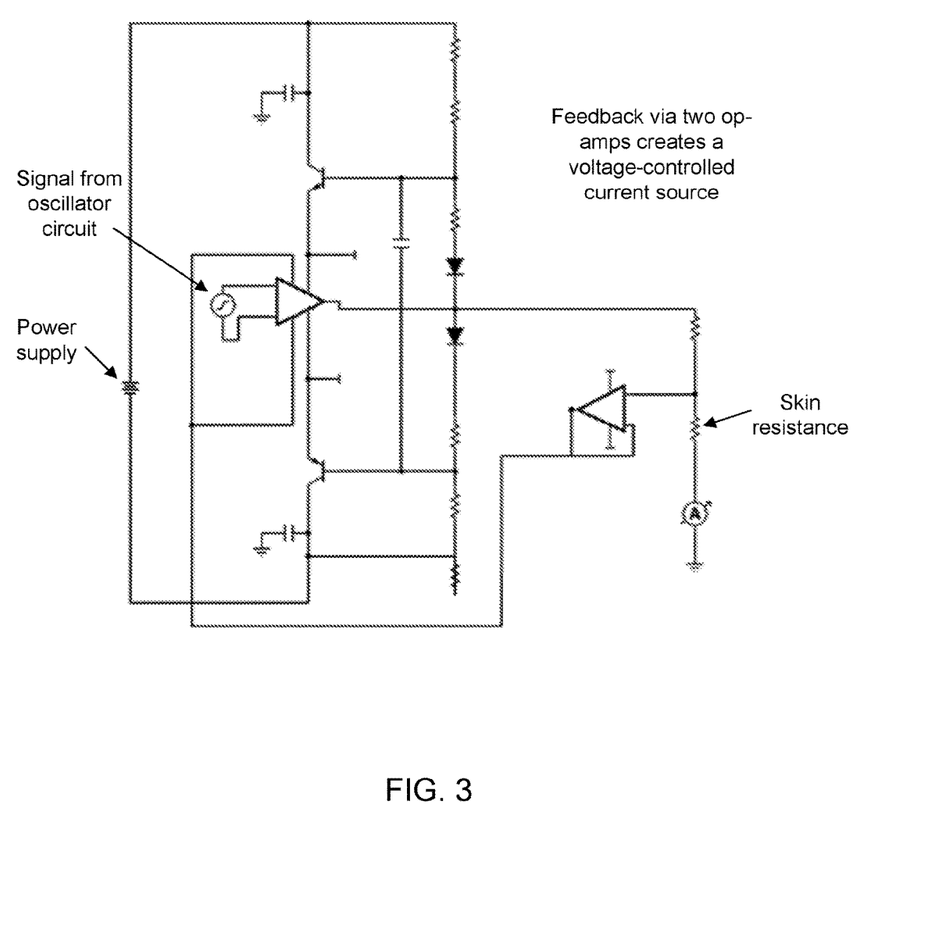
FIG. 3 illustrates current-control circuitry for an electronic nerve stimulation system in accordance with an example.

FIG. 3 illustrates an example of current-control circuitry for an electronic nerve stimulation system. The current-control circuitry can be included in a stimulation device of the electronic nerve stimulation system. The current-control circuitry can set a stimulation current amplitude in the 0-50 mA range across a resistance (e.g., skin/body) of 10Ω to 50 kΩ. As shown in FIG. 3, feedback via two operational amplifiers can create a voltage-controlled current source. The current-control circuitry can include a signal from an oscillator circuit and a power supply. In one example, the current-control circuitry can additionally function as impedance-testing circuitry.

Figure 4:
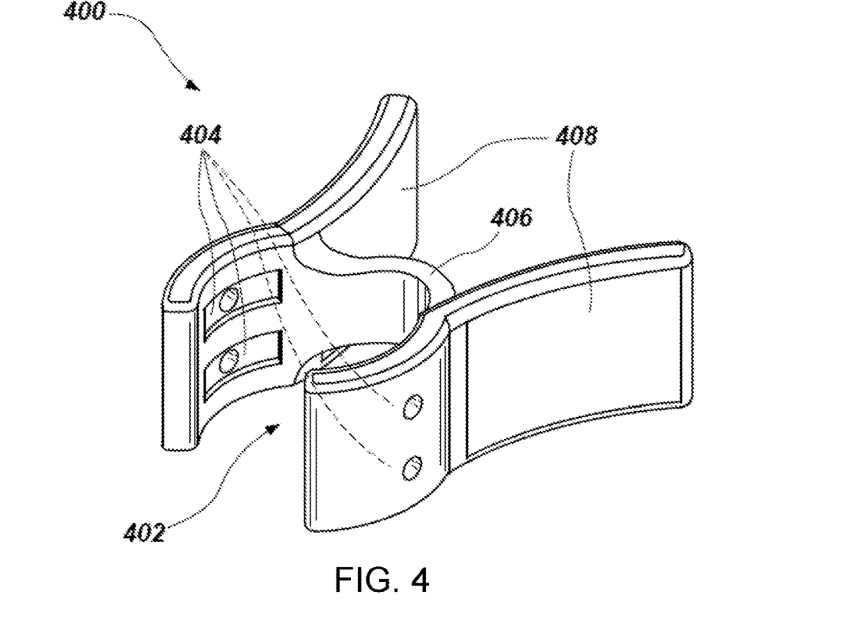
FIG. 4 illustrates an electrode for attachment to a subject's digit in accordance with an example.

In order to secure electrodes in a desired location, a mechanical support can be used to orient and secure electrodes adjacent target nerves. For example, FIG. 4 illustrates an exemplary electrode clip 400 for attachment to a subject's digit, such as a finger. The electrode clip 400 may be a resilient flexible member to allow universal fit, but in some cases can come in various sizes to fit a full range of human finger diameters. The electrode clip 400 can function similar to an alligator clip or a clothespin. The electrode clip 400 can include a stimulating area 402, a defined number of electrode slots 404, a bridge 406 and grips 408. As shown in FIG. 4, two halves around the stimulating area 402 can be expanded by pinching the electrode clip 400 via the grips 408, which can allow for the electrode clip 400 to be easily donned on the subject or removed from the subject. The subject's finger can be slid into the stimulating area 402. The defined number of electrode slots 404 can include a corresponding number of electrodes (e.g., four electrodes can be placed in four electrode slots). In other words, there can be one electrode per electrode slot 404.

In one example, two electrodes can function as a current source/sink pair. Current can travel from one electrode of the pair to the other electrode of the pair, and the current can affect a digital nerve that lies beneath the skin between the two electrodes. Two electrode pairs can be used in order to block nerve conduction on the two digital nerves that innervate any given fingertip. Current may not travel across a belly of the finger to the other two electrodes (i.e., a second current source/sink pair). In one example, the bridge 406 can function like a spring that compresses the two halves of the electrode clip 400, which causes the electrodes to be compressed over the skin covering the digital nerves. In addition, the electrode clip 400 can tightly fit over the finger to prevent the electrodes from lifting off the subject's skin.

Figure 5:
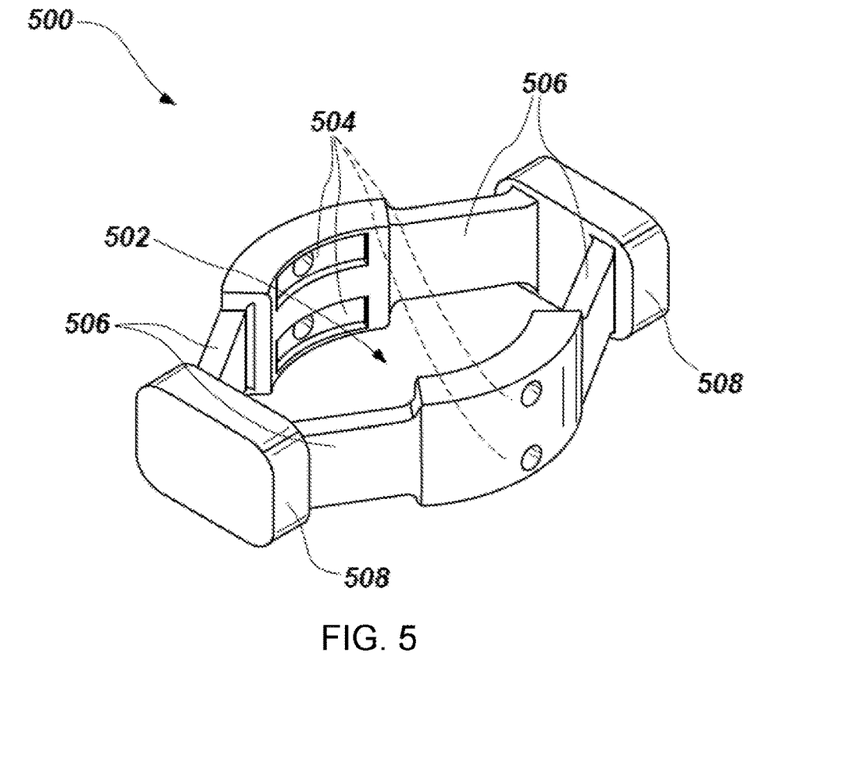
FIG. 5 illustrates an electrode for attachment to a subject's digit in accordance with an example.

FIG. 5 illustrates an electrode device 500 for attachment to a subject's digit, such as a toe. The electrode device 500 may be a universal size, although typically various sizes can more carefully accommodate a full range of human toe diameters. One target population for toe use is ingrown toenail procedures. The electrode device 500 can include a stimulating area 502, a defined number of electrode slots 504, a defined number of bridges 506 and grips 508. The electrode device 500 for toes may not use an alligator clip or clothespin design, as compared to the electrode clip 400 for usage with fingers. Due to the relatively small working area when working with toes, larger grips can interfere with the physician. In contrast, the electrode device 500 can use grips 508 on either side of the stimulating area 502. Four resiliently flexible bridges 506 can allow the electrode device 500 to apply a compression force around the stimulating area 502. By pinching the grips 508 together, the stimulating area 502 can expand thereby allowing the electrode device 500 to be slid across the toe and onto a base of the toe. When the grips 508 are released, the electrode device 500 can compress around to engage the base of the toe, which can create a tight electrode/skin interface. In addition, the design of the electrode device 500 can result in the grips 508 being mostly out of the way of the physician handling the electrode device 500.

In one example, the defined number of electrode slots 504 can include a corresponding number of electrodes (e.g., four electrodes can be placed in four electrode slots). In other words, there can be one electrode per electrode slot 504. Two electrodes can function as a current source/sink pair. Current can travel from one electrode of the pair to the other electrode of the pair, and the current can affect a digital nerve (and corresponding neuronal tissue) that lies beneath the skin between the two electrodes. Current may not travel across a belly of the finger to the other two electrodes (i.e., a second current source/sink pair).

In one example, electrode devices can be specifically designed for other locations of the body. For example, arm electrodes (placed over the ulnar nerve at the elbow) can be used for numbing the forearm and/or hand. Leg electrodes (placed over the medial crural saphenous nerve or lateral sural nerve) can be used for numbing skin over the calf muscles. Face electrodes (placed over the trigeminal nerve or nerve branches, e.g., on the cheeks and/or chin) can be used for numbing teeth and gums. In addition, additional electrode devices can be used for other nerve targets. The electrode device can include any number of electrodes, although as a general rule can range from 2 to 20 and often from 2 to 3. In some cases, the device can include a first electrode as a source, a second electrode as a sink, and a third electrode as a ground.

In one configuration, the electrode clip 400 and/or the electrode device 500 can produce high-frequency alternating current in a frequency range within 10-50 kHz and in a 0-50 milliamp mA range. The electrode clip 400 and/or the electrode device 500 can be directed to relatively superficial targets, such as the surface of the skin. Thus, the electrode clip 400 and/or the electrode device 500 can be non-invasive. The electrode clip 400 and/or the electrode device 500 can operate to block nerve transmissions for the subject. The electrode clip 400 and/or the electrode device 500 can be location-specific and can use location-specific stimulation patterns. For example, thin skin near the base of the finger has a lower resistance than near the elbow. The current needed to reach an underlying nerve and neuronal tissue target is lower in the finger than the elbow, and thus, the maximum current the stimulator would generate should be different for the finger and the elbow. Similar adjustments can be made based on locations and individual patient variations in skin resistance.

Figure 6:
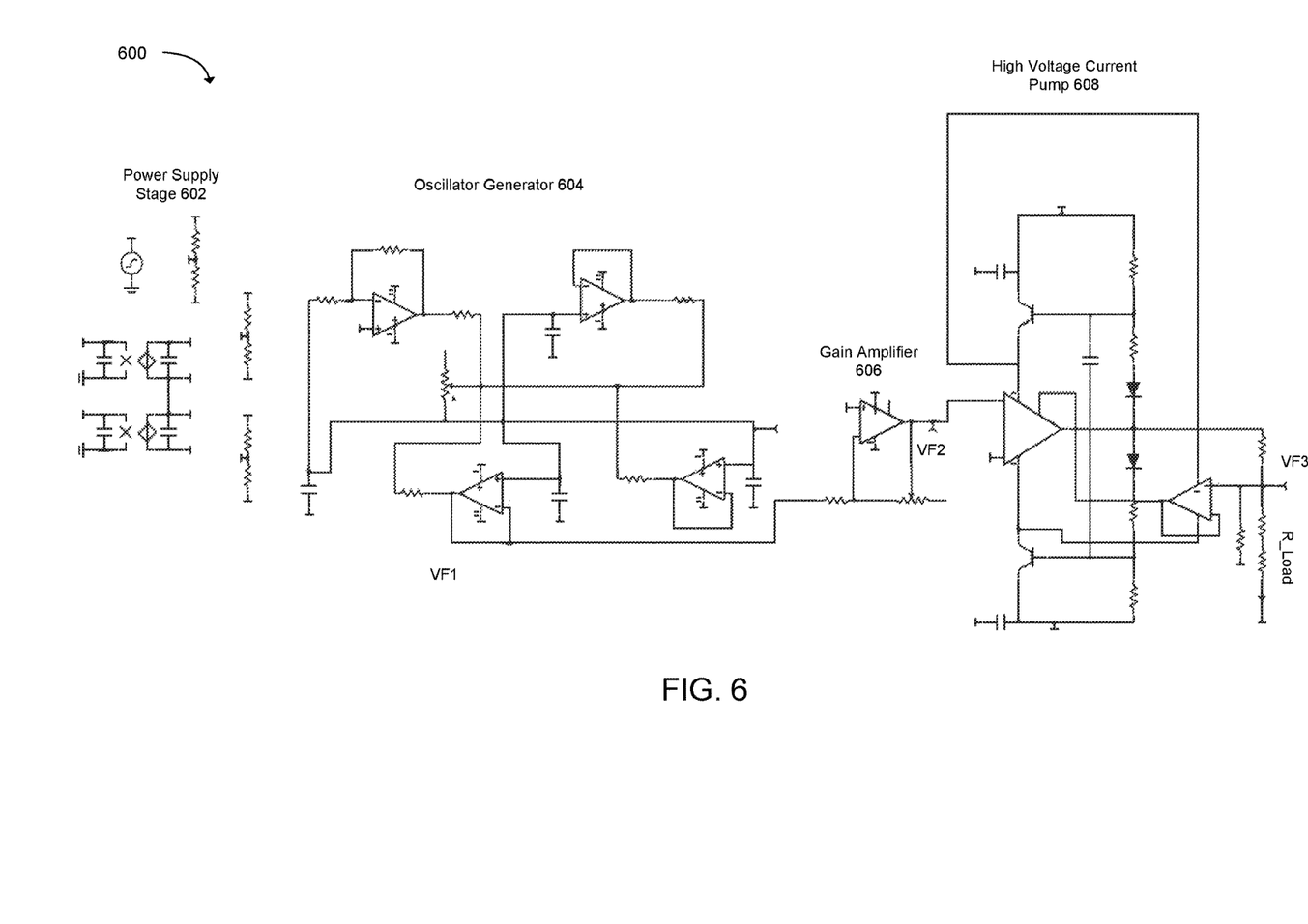
FIG. 6 illustrates a high frequency transcutaneous stimulator circuit in accordance with an example.

FIG. 6 illustrates an exemplary high frequency transcutaneous stimulator circuit 600. The high frequency transcutaneous stimulator circuit 600 can use a wall-connected 12 V AC-to-DC power supply and can output a sinusoidally varying, constant amplitude current waveform through a variable impedance load. A frequency and current waveform amplitude can be adjustable from approximately 9 k to 50 k Hz, and 0 to 20 mA, respectively, via potentiometers. The high frequency transcutaneous stimulator circuit 600 can include four main sections: a power supply stage 602, an oscillator generator 604, a gain amplifier 606 and a high voltage current pump 608 (e.g., a high voltage Howland current pump). Typically, the stimulator will not send treatment current immediately after it is powered on. The current can ramp from 0 mA to a treatment level, usually in the range of 1-30 mA, over the source of several seconds to several minutes to prevent the patient from feeling an electrical shock. Slowly adding current will slowly build a feeling of paresthesia, i.e. tingling, until treatment current has been reached, at which point a nerve block has been achieved.

In one example, a 12 V 16 W AC/DC adapter in the power supply stage 602 can be used to supply power to the high frequency transcutaneous stimulator circuit 600. The 12 V can be divided in half and a virtual ground can be created, using ±6 volt supplies for operational amplifiers in a next stage (i.e., the oscillator generator 604). Two DC/DC converters can be used in series to step the voltage from 12 V to ±160 V (by using the full range of 0 to 320 V and using a virtual ground at 160 V). In addition, further voltage dividers can be used to develop ±40 V to power the gain amplifier 606.

In one example, a quad operational amplifier single integrated circuit (IC) package (e.g., TL074) can be used to build the oscillator generator 604, which can output a sinusoidal waveform. A sine wave amplitude of the sinusoidal waveform can have a frequency adjustable between approximately 9 k and 50 k Hz via the potentiometer. The potentiometer can be connected in series with a 3 k resistor in each of the four stages of the oscillator generator 604. An output of a fourth operational amplifier can be tapped for a next stage in the high frequency transcutaneous stimulator circuit 600 (i.e., the gain amplifier 606), as the fourth operational amplifier can have increased stability and reduced distortion.

In the gain amplifier 606, an operational amplifier (e.g., OPA453) can be used in an inverting amplifier configuration to control an amplitude of the sine wave, from approximately 0 to 20 V. This inverting architecture can allow for a gain of 0. The actual inversion can be adequate as long as the waveform is symmetric about a mean. The amplified sine wave can directly control the amplitude of the current waveform in a next stage (i.e., the high voltage current pump 608) of the high frequency transcutaneous stimulator circuit 600.

The high voltage current pump 608 (e.g., a high voltage Howland current pump) can be realized with one or more amplifiers (e.g., INA149 and OPA140) to provide a voltage-to-current conversion, with the current amplitude set by the previous stage (i.e., the gain amplifier 606). While this architecture can be valuable for its ability to provide a constant current under a changing load, a common limitation is a low maximum current as a result of high load resistances. To resolve this limitation, bootstrapping can be used to operate operational amplifiers on a much wider voltage supply. In this bootstrapped configuration, the output voltage of an operational amplifier can be used to directly control its supply voltages. Therefore, the high voltage current pump 608 can produce the sinusoidally varying, constant amplitude current waveform.

As previously discussed, the sinusoidally varying, constant amplitude current waveform produced by the high frequency transcutaneous stimulator circuit 600 can be provided to one or more electrodes attached to a subject, which can result in the blocking of peripheral nerve transmission for the subject.

In one example, VF1, VF2, and VF3 can be recommended measurement points for testing the high frequency transcutaneous stimulator circuit 600. In addition, R_Load can be a model of a patient's skin impedance. Each side of the R_Load can be connected to an electrode contact.

Figure 7:
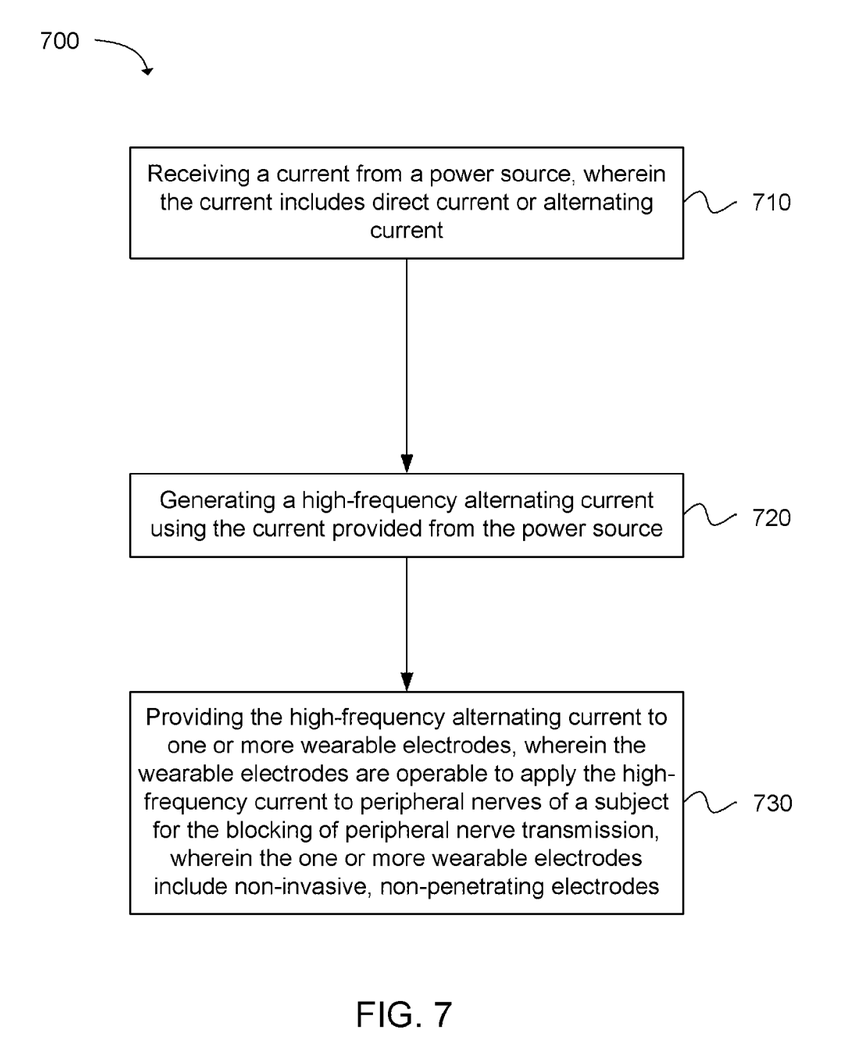
FIG. 7 depicts a flow chart of a method for electronically blocking peripheral nerve transmission in accordance with an example.

FIG. 7 depicts a flow chart of an exemplary method for electronically blocking peripheral nerve transmission. The method can include the operation of receiving a current from a power source, wherein the current includes direct current or alternating current, as in block 710. The method can include the operation of generating a high-frequency alternating current using the current provided from the power source, as in block 720. The method can include the operation of providing the high-frequency alternating current to one or more wearable electrodes, as in block 730. The wearable electrodes can be operable to apply the high-frequency current to peripheral nerves to stimulate neuronal tissue of a subject for the blocking of peripheral nerve transmission. The one or more wearable electrodes can include non-invasive, non-penetrating electrodes.

Figure 8:
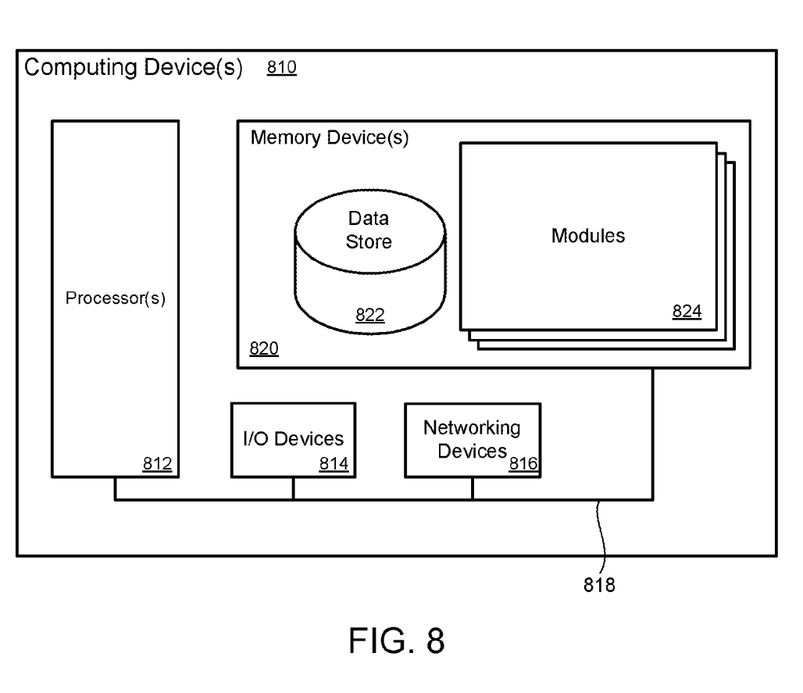
FIG. 8 is a block diagram that provides an example illustration of a computing device that may be employed in the present technology.

FIG. 8 illustrates a computing device 810 on which modules of this technology may execute. A computing device 810 is illustrated on which a high level example of the technology may be executed. The computing device 810 may include one or more processors 812 that are in communication with memory devices 820. The computing device 810 may include a local communication interface 818 for the components in the computing device. For example, the local communication interface 818 may be a local data bus and/or any related address or control busses as may be desired.

The memory device 820 may contain modules 824 that are executable by the processor(s) 812 and data for the modules 824. The modules 824 may execute functions that perform the methods described earlier. A data store 822 may also be located in the memory device 820 for storing data related to the modules 824 and other applications along with an operating system that is executable by the processor(s) 812.

Other applications may also be stored in the memory device 820 and may be executable by the processor(s) 812. Components or modules discussed in this description that may be implemented in the form of software using high programming level languages that are compiled, interpreted or executed using a hybrid of the methods.

The computing device may also have access to I/O (input/output) devices 814 that are usable by the computing devices. Networking devices 816 and similar communication devices may be included in the computing device. The networking devices 816 may be wired or wireless networking devices that connect to the internet, a LAN, WAN, or other computing network.

The components or modules that are shown as being stored in the memory device 820 may be executed by the processor(s) 812. The term "executable" may mean a program file that is in a form that may be executed by a processor 812. For example, a program in a higher level language may be compiled into machine code in a format that may be loaded into a random access portion of the memory device 820 and executed by the processor 812, or source code may be loaded by another executable program and interpreted to generate instructions in a random access portion of the memory to be executed by a processor. The executable program may be stored in any portion or component of the memory device 820. For example, the memory device 820 may be random access memory (RAM), read only memory (ROM), flash memory, a solid state drive, memory card, a hard drive, optical disk, floppy disk, magnetic tape, or any other memory components.

The processor 812 may represent multiple processors and the memory device 820 may represent multiple memory units that operate in parallel to the processing circuits. This may provide parallel processing channels for the processes and data in the system. The local interface 818 may be used as a network to facilitate communication between any of the multiple processors and multiple memories. The local interface 818 may use additional systems designed for coordinating communication such as load balancing, bulk data transfer and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, non-transitory media such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. An electronic nerve stimulation system, comprising:
   a stimulation device operable to generate a high-frequency alternating current; and
   one or more wearable electrodes operable to apply the high-frequency alternating current from the stimulation device to peripheral nerves to provide an electrical stimulation, wherein the one or more wearable electrodes interface with the stimulation device via a connection system, wherein the stimulation device is further operable to implement a pre-programmed frequency modulation pattern when generating the high-frequency alternating current.

2. The electronic nerve stimulation system of claim 1, wherein the stimulation device is further operable to generate the high-frequency alternating current to be a waveform ranging from 10 to 50 kilohertz (kHz).

3. The electronic nerve stimulation system of claim 1, wherein the stimulation device is further operable to generate the high-frequency alternating current to be a waveform in a 0-50 milliamp (mA) range, wherein the high-frequency alternating current is applied across a skin or body resistance of 10 ohms ($\Omega$) to 50 kilo-ohms (k$\Omega$).

4. The electronic nerve stimulation system of claim 1, wherein the high-frequency alternating current is applied to peripheral nerves that are less than two centimeters (cm) from a skin surface.

5. The electronic nerve stimulation system of claim 1, further comprising a power supply that provides direct current or alternating current to the stimulation device for generation of the high-frequency alternating current.

6. The electronic nerve stimulation system of claim 1, further comprising a user interface that enables adjustment of at least one of a frequency and amplitude of the high-frequency alternating current.

7. The electronic nerve stimulation system of claim 1, wherein the stimulation device is portable.

8. The electronic nerve stimulation system of claim 1, wherein the wearable electrodes are shaped to align with peripheral nerves in a target nerve location.

9. The electronic nerve stimulation system of claim 1, wherein the high-frequency alternating current is applied to the peripheral nerves to cause at least one of the following: pain blocking, sensation blocking and muscle activation.

10. The electronic nerve stimulation system of claim 1, wherein the wearable electrodes are at least one of: non-invasive, non-penetrating electrodes or minimally-invasive, penetrating electrodes.

11. The electronic nerve stimulation system of claim 1, wherein the stimulation device includes impedance testing circuitry, safety analysis circuitry, fault-detection circuitry and ground-isolation circuitry.

12. The electronic nerve stimulation system of claim 1, wherein the stimulation device is operable to generate the high-frequency alternating current via current-control circuitry that includes an amplifier, an oscillator circuit, a rectifier and a smoothing filter.

13. The electronic nerve stimulation system of claim 1, wherein the stimulation device is operable to generate the high-frequency alternating current via current-control circuitry in which feedback via two operational amplifiers creates a voltage-controlled current source.

14. The electronic nerve stimulation system of claim 1, wherein the wearable electrodes include at least one of: finger electrodes, toe electrodes, arm electrodes, leg electrodes, face electrodes, neck electrodes and penis electrodes.

15. The electronic nerve stimulation system of claim 1, wherein the stimulation device is operable to generate the high-frequency alternating current via high frequency transcutaneous circuitry that includes a power supply, an oscillator generator, a gain amplifier and a high voltage current pump.

16. A system for blocking peripheral nerve transmission, the system comprising:
   a power source;
   a stimulation device operable to generate a high-frequency alternating current using current provided from the power source, wherein the stimulation device is operable to generate the high-frequency alternating current via high frequency transcutaneous circuitry that includes a power supply, an oscillator generator, a gain amplifier and a high voltage current pump; and
   one or more wearable electrodes communicatively coupled to the simulation device via lead wires and connectors, wherein the wearable electrodes are operable to apply the high-frequency alternating current received from the stimulation device to peripheral nerves of a subject for the blocking of peripheral nerve transmission, wherein the one or more wearable electrodes include non-invasive, non-penetrating electrodes.

17. The system of claim 16, wherein the stimulation device is operable to generate the high-frequency alternating current to be a sinusoidally varying, constant amplitude current waveform through a variable impedance load.

18. The system of claim 16, wherein the stimulation device is operable to generate the high-frequency alternating current to be adjustable from 9 k to 50 k hertz (Hz) and from 0 to 20 milliamps (mA) via potentiometers.

19. The system of claim 16, wherein the power source provides direct current or alternating current to the stimulation device for generation of the high-frequency alternating current, wherein the direct current or alternating current is provided via batteries or via a wall-plug adapter or via both batteries and wall-plug adapter.

20. The system of claim 16, wherein the one or more wearable electrodes are not surgically implanted in the subject.

21. A method for electronically blocking peripheral nerve transmission, the method comprising:
   receiving a current from a power source, wherein the current includes direct current or alternating current;
   generating a high-frequency alternating current using the current provided from the power source, wherein the high-frequency alternating current is generated using a pre-programmed frequency modulation pattern; and
   providing the high-frequency alternating current to one or more wearable electrodes, wherein the wearable electrodes are operable to apply the high-frequency current to peripheral nerves to stimulate neuronal tissue of a subject for the blocking of peripheral nerve transmission, wherein the one or more wearable electrodes include non-invasive, non-penetrating electrodes.

22. The method of claim 21, wherein the high-frequency alternating current is generated to be a sinusoidally varying, constant amplitude current waveform through a variable impedance load.

23. The method of claim 21, wherein the high-frequency alternating current is generated to be adjustable from 9 k to 50 k hertz (Hz) and from 0 to 20 milliamps (mA) via potentiometers.

* * * * *